(12) United States Patent
Hariri

(10) Patent No.: US 12,311,548 B2
(45) Date of Patent: *May 27, 2025

(54) ESTIMATING JOINT FRICTION AND TRACKING ERROR OF A ROBOTICS END EFFECTOR

(71) Applicant: Verb Surgical Inc., Santa Clara, CA (US)

(72) Inventor: Alireza Hariri, Berkeley, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,770

(22) Filed: May 31, 2023

(65) Prior Publication Data

US 2024/0066693 A1    Feb. 29, 2024

Related U.S. Application Data

(63) Continuation of application No. 17/959,718, filed on Oct. 4, 2022, now Pat. No. 11,697,207, which is a (Continued)

(51) Int. Cl.
*B25J 9/16*        (2006.01)

(52) U.S. Cl.
CPC ........... *B25J 9/1653* (2013.01); *B25J 9/1664* (2013.01)

(58) Field of Classification Search
CPC ...... B25J 9/1653; B25J 9/1664; B25J 9/1689; A61B 34/71; A61B 34/30;
(Continued)

(56) References Cited

U.S. PATENT DOCUMENTS 9,581,190 B2    2/2017 Richman
10,166,082 B1   1/2019 Hariri et al.
(Continued)

FOREIGN PATENT DOCUMENTS

CN    101340850 A    1/2009
CN    104400783 A    3/2015
(Continued)

OTHER PUBLICATIONS

Office Action received for Chinese Patent Application No. 202080042085.3, mailed on Feb. 27, 2024, 18 pages (7 pages of English Translation and 11 pages of Original Document).
(Continued)

*Primary Examiner* — Robert T Nguyen
(74) *Attorney, Agent, or Firm* — Aikin & Gallant, LLP

(57) ABSTRACT

A computerized method for estimating joint friction in a joint of a robotic wrist of an end effector. Sensor measurements of force or torque in a transmission that mechanically couples a robotic wrist to an actuator, are produced. Joint friction in a joint of the robotic wrist that is driven by the actuator is computed by applying the sensor measurements of force or torque to a closed form mathematical expression that relates transmission force or torque variables to a joint friction variable. A tracking error of the end effector is also computed, using a closed form mathematical expression that relates the joint friction variable to the tracking error. Other aspects are also described and claimed.

20 Claims, 5 Drawing Sheets

Related U.S. Application Data continuation of application No. 16/893,315, filed on Jun. 4, 2020, now Pat. No. 11,478,928.

(60) Provisional application No. 62/858,937, filed on Jun. 7, 2019.

(58) Field of Classification Search
CPC ........ A61B 2034/302; A61B 2034/306; A61B 2090/064; A61B 2090/066; A61B 34/74; G05B 2219/37373; G05B 2219/45118
See application file for complete search history.

(56) References Cited

U.S. PATENT DOCUMENTS

| | | | |
|---|---|---|---|
| 11,161,243 B2 | 11/2021 | Rabindran et al. | |
| 11,478,928 B2* | 10/2022 | Hariri | B25J 9/1664 |
| 11,697,207 B2* | 7/2023 | Hariri | A61B 34/30 |
| | | | 700/254 |
| 12,172,325 B2* | 12/2024 | Zhang | B25J 9/1674 |
| 2007/0151390 A1 | 7/2007 | Blumenkranz et al. | |
| 2010/0243344 A1 | 9/2010 | Wyrobek et al. | |
| 2014/0156074 A1* | 6/2014 | Seo | B25J 3/04 |
| | | | 700/257 |
| 2016/0338784 A1 | 11/2016 | Hatakeyama et al. | |
| 2020/0387053 A1 | 12/2020 | Hong | |
| 2021/0045820 A1 | 2/2021 | Asadian et al. | |
| 2021/0045827 A1 | 2/2021 | Asadian et al. | |
| 2021/0162596 A1* | 6/2021 | Clever | B25J 9/1633 |
| 2021/0282876 A1 | 9/2021 | Ergueta et al. | |
| 2022/0047347 A1 | 2/2022 | Maughan et al. | |
| 2022/0082206 A1 | 3/2022 | Walker et al. | |
| 2022/0233271 A1* | 7/2022 | Peine | A61B 90/06 |
| 2023/0046044 A1 | 2/2023 | Zhang et al. | |
| 2023/0173678 A1* | 6/2023 | Monreal | G01L 5/28 |
| | | | 700/245 |
| 2024/0033929 A1* | 2/2024 | Lamy | B25J 9/1689 |

FOREIGN PATENT DOCUMENTS

| | | |
|---|---|---|
| CN | 105979850 A | 9/2016 |
| CN | 109249397 A | 1/2019 |
| CN | 108638072 B | 7/2021 |
| WO | 2016/110320 A1 | 7/2016 |

OTHER PUBLICATIONS

Hardeman, T., et al., "Modelling and identification of industrial robots including drive and joint flexibilities" 2008.

International Preliminary Report on Patentability received for PCT Patent Application No. PCT/US20/36487, mailed on Dec. 16, 2021, 5 pages.

International Search Report and Written Opinion received for PCT Patent Application No. PCT/US20/36487, mailed on Sep. 10, 2020, 5 pages.

Supplementary European Search Report and Search Opinion received for European Application No. 20819330, mailed on Jun. 6, 2023, 10 pages.

Chinese Patent No. 202080042085.3, "The Second Office Action and Search Report", Mailed Aug. 28, 2024, 15 pages.

* cited by examiner

ESTIMATING JOINT FRICTION AND TRACKING ERROR OF A ROBOTICS END EFFECTOR

CROSS-REFERENCE TO RELATED APPLICATIONS

This application is a continuation of U.S. patent application Ser. No. 17/959,718, filed Oct. 4, 2022, entitled "ESTIMATING JOINT FRICTION AND TRACKING ERROR OF A ROBOTICS END EFFECTOR," which is a continuation of U.S. patent application Ser. No. 16/893,315, filed Jun. 4, 2020, now U.S. Pat. No. 11,478,928, issued Oct. 25, 2022, which claims the benefit of the earlier filing date of U.S. Provisional Application No. 62/858,937, filed Jun. 7, 2019.

FIELD

Embodiments related to robotic systems are disclosed. More particularly, embodiments related to surgical robotic systems and techniques for estimating joint friction and tracking error for the end effector of a surgical robotic tool are disclosed.

BACKGROUND INFORMATION

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to control a robotically-assisted tool located at an operating table. The surgeon may use a computer console located in the operating room, or it may be located in a different city, to command a robot to manipulate the surgical tool mounted on the operating table. The robotically-controlled surgical tool can be a grasper mounted on a robotic arm. Accordingly, the surgical robotic system may be controlled by the remote surgeon to grasp tissue during a robotic surgery.

Control of the surgical robotic system may require control inputs from the surgeon. For example, the surgeon may hold in her hand a user input device, UID, such as a joystick or a computer mouse that she manipulates to generate the signals for the control commands that drive actuators and thereby control motion of the surgical robotic system components, e.g., a robotic arm, and/or a surgical tool including its end effector that is attached to the arm.

SUMMARY

There may be a tracking error between a commanded position x1 (generated in part from a current state or pose of the UID) at an actuator, and a controlled position (e.g., angle) x2 of an end effector that is mechanically coupled to the actuator through a transmission (so as to be driven by the actuator). It is demonstrated below in detail how the tracking error may be mathematically estimated (e.g., computed by a programmed processor), based on values of i) mechanical compliance (or equivalently stiffness or elasticity) of the transmission and ii) joint friction that may resist the commanded motion of the end effector.

Another aspect of the disclosure here is a method for estimating (e.g., computing) joint friction, or friction forces, in the joints of a robotic wrist, based on measurements of force through the transmission that couples the robotic wrist to its actuator (e.g., cable force measurements, representing tension in the cable). The estimated joint friction may then be used in estimating the tracking error of the end effector.

In one aspect, a problem to be solved is how to determine (e.g., estimate) the amount of joint friction, and then how to use that estimated joint friction together with for example a known (e.g., assumed) tool compliance or elasticity to estimate the tracking error of a controlled end effector. Solutions to such a problem help the designer of a surgical robotic system to understand and reduce as needed the tracking error. This may be done by the designer selecting suitable values for the transmission stiffness (e.g., greater cable stiffness), or seeking ways to reduce friction torques in the robotic wrist (e.g., by lubrication or by using different materials.)

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

In various embodiments, description is made with reference to figures. However, certain embodiments may be practiced without one or more of these specific details, or in combination with other known methods and configurations. The embodiments of the invention are thus illustrated by way of example and not by way of limitation in the figures in which like references indicate similar elements. It should be noted that references to "an" or "one" embodiment of the invention or aspect of this disclosure are not necessarily to the same embodiment or aspect, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from an operator. Similarly, "proximal" may indicate a location in a second direction opposite to the first direction, e.g., toward the operator. Such terms are provided to establish relative frames of reference, however, and are not intended to limit the use or orientation of a device to a specific configuration described in the various embodiments below.

Figure 1:
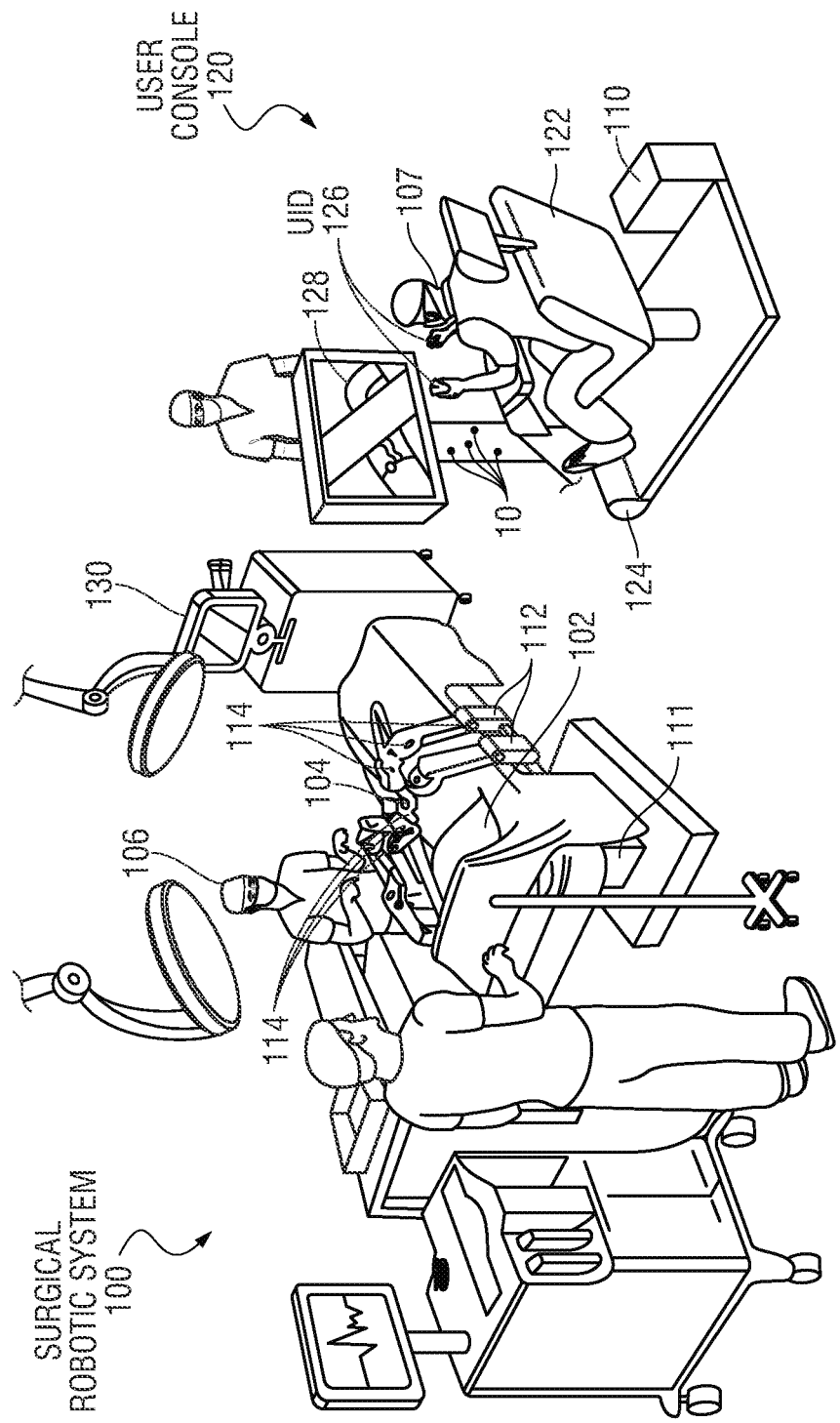
FIG. 1 is a pictorial view of an example surgical robotic system 100 in an operating arena.

FIG. 1 is a pictorial view of an example surgical robotic system 100 in an operating arena. The robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may include an end effector that is attached to a distal end of a surgical arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 is a grasper that can grasp tissue of patient 102. Surgical tool 104 may be controlled manually, by a bedside operator 106; or it may be controlled robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user input devices, UIDs 126, and at least one operator display 128 configured to display, for example, a view of the surgical site inside patient 102. In the example user console 120, remote operator 107 is sitting in seat 122 and viewing the operator display 128 while manipulating a foot-operated control 124 and a handheld UID 126 in order to remotely control the arms 112 and surgical tools 104 (that are mounted on the distal ends of the arms 112). Foot-operated control(s) 124 can be foot pedals, such as seven pedals, that generate motion control signals when actuated. User console 120 may include one or more additional input devices, such as a keyboard or a joystick, to receive manual inputs to control operations of user console 120 or surgical robotic system 100.

In some variations, bedside operator 106 may also operate system 100 in an "over the bed" mode, in which bedside operator 106 is now at a side of patient 102 and is simultaneously manipulating a robotically-driven tool (its end effector, attached to arm 112), e.g., with a handheld UID 126 held in one hand, and a manual laparoscopic tool. For example, the bedside operator's left hand may be manipulating the handheld UID 126 to control a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion, and administered anesthesia. Initial access to the patient anatomy can be achieved using known techniques, such as by forming an incision in the skin. A trocar and/or other surgical tool can be inserted into the incision through the optical entry in the patient. The trocar can then be positioned at the surgical site (inside the body of the patient). Initial access to the surgical site may be performed manually while the arms of the robotic system 100 are in a stowed configuration or withdrawn configuration (to facilitate access to the surgical site) or in an operator-defined parking pose. Once initial access is completed, initial positioning or preparation of the robotic system including docking the arms 112 to their trocars, respectively, and attaching tools (having end effectors) to the arms 112, respectively, may be performed. Next, the surgery proceeds with the remote operator 107 at the user console 120 utilizing the foot-operated controls 124 and the UIDs 126 to manipulate the various end effectors and perhaps an imaging system, to perform the surgery. Manual assistance may also be provided at the procedure bed or table, by sterile-gowned bedside personnel, e.g., bedside operator 106 who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move a robot arm actuator 114 in robotic system 100. UID 126 may be communicatively coupled to the rest of robotic system 100, e.g., via a console computer system 110. UID 126 can generate spatial state signals corresponding to movement of UID 126, e.g., position and orientation of the handheld housing of the UID, and the spatial state signals may be input signals to control a motion of the robot arm actuator 114. Robotic system 100 may produce control signals as a function of the spatial state signals, to control proportional motion of actuator 114. In one embodiment, a console processor of console computer system 110 receives the spatial state signals and generates the corresponding control signals. Based on these control signals, which control how the actuator 114 is energized to move a segment or link of arm 112, the movement of a corresponding surgical tool including an end effector that is attached to the arm may mimic the movement of UID 126. Similarly, interaction between remote operator 107 and UID 126 can generate, for example, a grip control signal that drives an actuator in the arm 112 which in turn causes a jaw of a grasper of the surgical tool (that is attached to the arm 112) to close and grip the tissue of patient 102.

The sensed motion of UID 126 may alternatively be provided to control other aspects of surgical robotic system 100. For example, gestures detected by a finger clutch may generate a clutch signal to pause the motion of actuator 114 and the corresponding surgical tool 104. For example, when an operator touches the finger clutch of UID 126 with a finger, the finger clutch may generate a clutch signal, and the clutch signal may be an input signal to pause the motion of actuator 114. Similarly, one or more capacitive sensing pads may be located on UID 126, and the operator may touch the capacitive sensing pads to control a camera view of an endoscope, a cursor on a display of user console 120, etc., while performing a diagnostic, surgical, laparoscopic, or minimally invasive surgical procedure, or another robotic procedure.

Surgical robotic system 100 may include several UIDs 126 where respective control signals are generated for each UID that control the actuators and the surgical tool (end effector) of a respective arm 112. For example, remote operator 107 may move a first UID 126 to control the motion of actuator 114 that is in a left robotic arm, where the actuator responds by moving linkages, gears, etc., in that arm 112. Similarly, movement of a second UID 126 by remote operator 107 controls the motion of another actuator 114, which in turn moves other linkages, gears, etc., of the robotic system 100. Robotic system 100 may include a right arm 112 that is secured to the bed or table to the right side of the patient, and a left arm 112 that is at the left side of the patient. An actuator 114 may include one or more motors, for example housed in the arm including within a tool drive housing on the arm 112. A mechanical transmission (partly in the arm 112 and in particular in the tool drive housing, and partly in a housing of the surgical tool) couples the actuator motors to the joints of the end effector. The actuator motors are controlled so that they drive the rotation of the joints of the end effector to change an orientation of the grasper (part of the end effector). Motion of several actuators 114 in the same arm 112 can be controlled by the spatial state signals generated from a particular UID 126. UIDs 126 can also be used to translate a finger squeeze into a corresponding motion of the jaws of the grasper. For example, a UID 126 can generate a grip signal to control motion of an actuator, e.g., a linear actuator, that opens or closes jaws of the grasper (that is at a distal end of the surgical tool) to grip tissue within patient 102.

In some aspects, the communication between platform 111 and user console 120 may be through a control tower 130, which may translate operator commands that are received from user console 120 (and more particularly from console computer system 110) into robotic control commands that are transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Tracking Error

Figure 2:
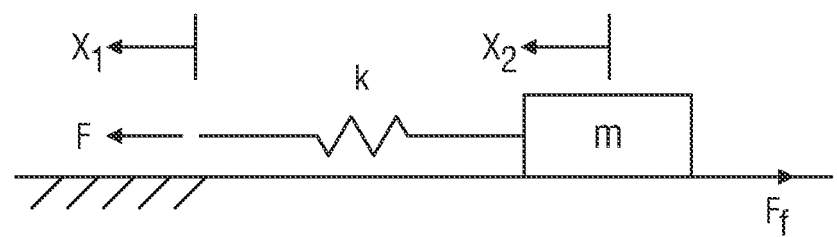
FIG. 2 illustrates the concept of tracking error using an example simple mechanical system having friction and compliance.

Referring now to FIG. 2, this figure is used to illustrate the concept of tracking error. It depicts an example, simple system where a force F is pulling mass m through a cable having stiffness k. The friction between mass and the ground is Ff, and assume that speed is constant (or mass m is negligible compared to F and Ff). As a result, this yields F=Ff. The tracking error between commanded position (x1) and controlled position (x2) is e=x1−x2, which is essentially equal to the cable (spring) elongation. Therefore, the tracking error may be given by e=Ff/k (ignoring external and inertial forces on the mass). This means that the following can be implied: error is proportional to friction; error is inversely proportional to stiffness; and if friction is zero (Ff=0), or stiffness is infinite (the cable is rigid), then tracking error is essentially zero e=0 and in the absence of friction, external load (applied on m) can play the same role as friction. In such a case, in order to reduce the tracking error one should focus on increasing stiffness, k.

Some Equations

Figure 3A:
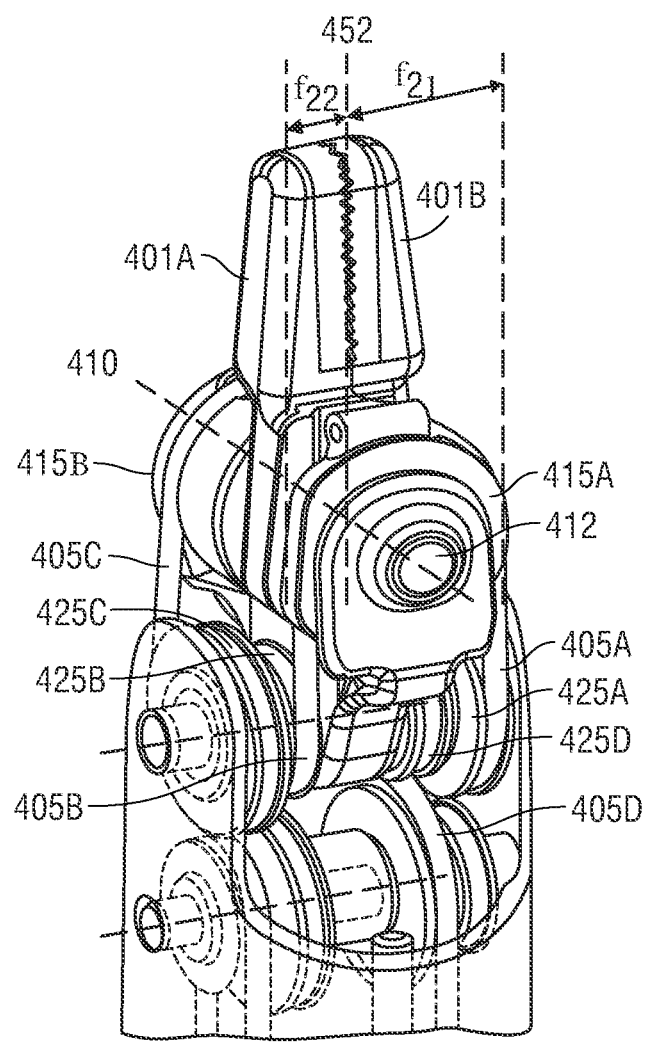
FIG. 3A and FIG. 3B depict an example robotic end effector that comprises a pair of jaws at a robotic wrist (for pitch degree of freedom), in closed and open states, respectively.
Figure 3B:
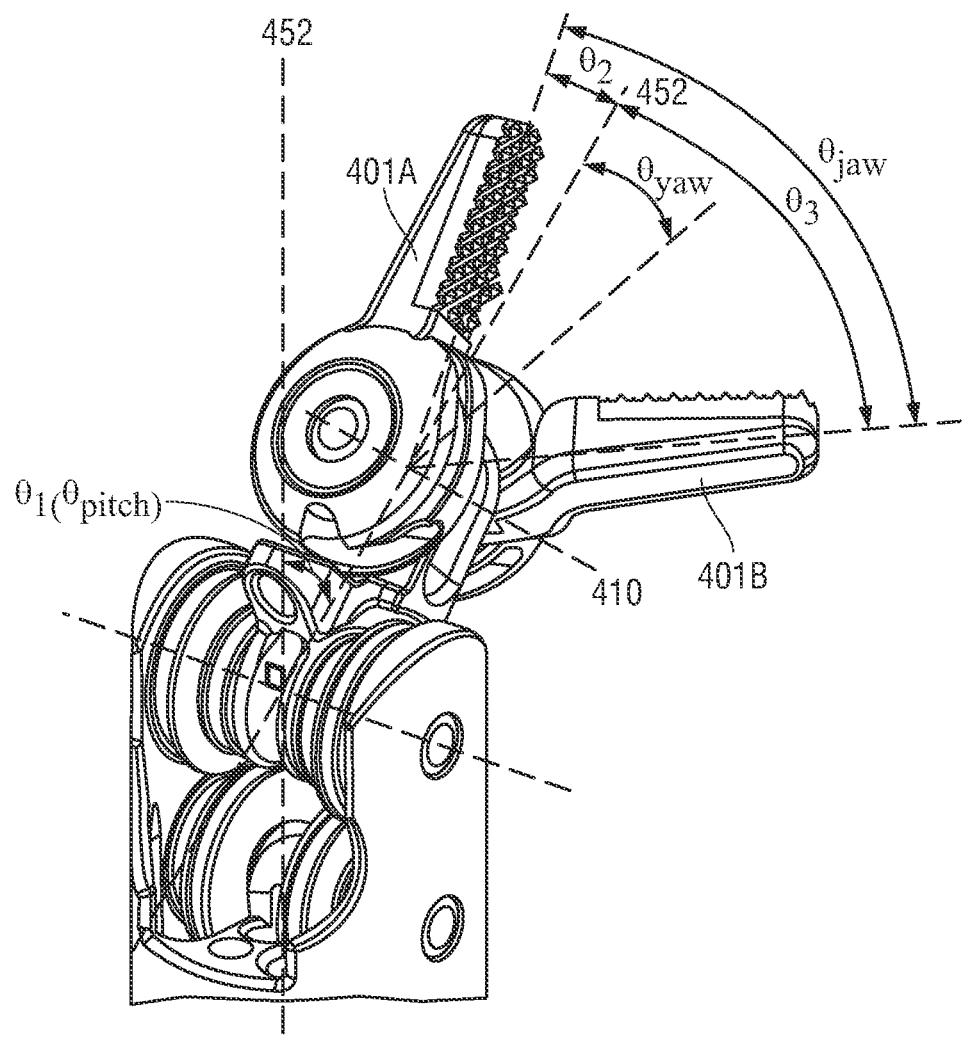

In order to perform control tasks (by a microprocessor configured or programmed to do so according to instructions stored in a computer-readable storage medium such as microelectronic memory) to control movement of an end effector, it is often beneficial to define a consistent coordinate frame for the joint angles of the end effector that are involved in such movement. For example, consider the example end effector that includes a robotic wrist coupled to two jaws of a grasper as shown in FIG. 3A and FIG. 3B, and which is described in more detail in U.S. Pat. No. 10,166,082 which is incorporated by reference herein. The jaws pivot about an axis 410 where the jaw angle ($\theta_{jaw}$) may be defined as the angle between the two jaws 401A and 401B, and the yaw angle ($\theta_{yaw}$) as the angle between the axis 452 and the line bisecting the jaw angle. Therefore:

$$\begin{cases} \theta_{pitch} = \theta_1 \\ \theta_{yaw} = \frac{1}{2}(\theta_2 + \theta_3) \\ \theta_{jaw} = \theta_2 - \theta_3 \end{cases} \quad (1)$$

The transformation between angles in FIG. 3B and these newly defined angles are as follows:

$$\begin{bmatrix} \theta_{pitch} \\ \theta_{yaw} \\ \theta_{jaw} \end{bmatrix} = D \cdot \begin{bmatrix} \theta_1 \\ \theta_2 \\ \theta_3 \end{bmatrix} \quad (2.a)$$

$$D = \begin{bmatrix} 1 & 0 & 0 \\ 0 & 1/2 & 1/2 \\ 0 & 1 & -1 \end{bmatrix} \quad (2.b)$$

We call this newly defined coordinate system, the extrinsic joint angles. Furthermore, the following nomenclature can be established for pulley geometries:
a) $r_{l1}$ is the radius of the outer pulleys 425A and 425C on which cables 405A and 405C are residing, respectively;
b) $r_{l2}$ is the radius of the inner pulleys 425B and 425D on which cables 405B and 405D are residing, respectively ($r_{l1}$ may or may not be equal to $r_{l2}$);

c) $r_{21}$ is the radius of pulley 415A on the side that cable 405A is residing (with reference to the center of pulley 415A and axle 412 as shown in FIG. 3A);

d) $r_{22}$ is the radius of pulley 415A on the side that cable 405B is residing (with reference to the center of pulley 415A and axle 412 as shown in FIG. 3A);

e) $r_{31}$ is the radius of pulley 415B on the side that cable 405C is residing; and f) $r_{32}$ is the radius of pulley 415B on the side that cable 405D is residing.

While in the above example the design is symmetrical, $r_{31}=r_{21}$, $r_{32}=r_{22}$ and $r_{21} \ne r_{22}$ (as shown in FIG. 3A), in some other designs it is possible to have $r_{31}=r_{21}=r_{32}=r_{22}$, as wells as $r_{11}=r_{12}$.

The following equation relates cable tensions or forces in the transmission, Zeta, ($\xi_{[4 \times 1]}$) to joint torques, Tau, ($\tau_{[3 \times 1]}$)

$$TaU_{[3 \times 1]} = B_{[3 \times 4]} \cdot Zeta_{[4 \times 1]} \quad (3)$$

where matrix (B) has the following form $$B_{[3 \times 4]} = \begin{bmatrix} -r_{11} & -r_{12} & r_{11} & r_{12} \\ -r_{21} & r_{22} & 0 & 0 \\ 0 & 0 & r_{31} & -r_{32} \end{bmatrix} \quad (4)$$

and ($\xi_1, \xi_2, \xi_3, \xi_4$) corresponds to cable tensions on cables 405A, 405B, 405C and 405D, respectively.

In Eq. (3), ($\tau_{[3 \times 1]}$) is the vector of virtual joint torques applied by the cables, which may cause the joints that are shown FIG. 3a and FIG. 3b to overcome friction and move against the external forces (that may be present on the end effector). Vector ($\tau_{[3 \times 1]}$) has three components:

$$\tau_{[3 \times 1]} = [\tau_1 \tau_2 \tau_3]^T \quad (6)$$

where ($\tau_1$) is the pitch joint torque, and ($\tau_2$) and ($\tau_3$) are the joint torques of jaw 401A and jaw 401B, respectively.

The kinematic relationship that relates the ideal cable displacements (assuming no cable elasticity) and jaw angles are as follows:

$$q_{[4 \times 1]} = [q_1 q_2 q_3 q_4]^T = B^T \cdot \theta_{[3 \times 1]} \quad (7)$$

where ($q_{[4 \times 1]}$) is the four-element vector containing the ideal displacements of cables 405A-405D, and ($\theta_{[3 \times 1]}$) is the vector of angles illustrated in FIG. 3B:

$$\theta_{[3 \times 1]} = [\theta_1 \theta_2 \theta_3]^T \quad (8)$$

In the actual case, where the cables are elastic, the actual and ideal cable displacements are related as follows:

$$\xi_{[4 \times 1]} = k(x_{[4 \times 1]} - B^T \cdot \theta_{[3 \times 1]}) \quad (9)$$

Where $\xi_{[4 \times 1]}$ is cable tensions, k is the elastic constant of the cables in N/m (assuming all cables are similar) and $(x_{[4 \times 1]} - B^T \cdot \theta_{[3 \times 1]})$ is the difference between actual cable displacements $x_{[4 \times 1]}$ and ideal cable displacements $B^T \cdot \theta_{[3 \times 1]}$.

Tracking Error as a Function of Friction and Stiffness

From eq. (7), we get:

$$\theta_{[3 \times 1]} = B^{-T} \cdot q_{[4 \times 1]} \quad (10)$$

Using the hooks law for each of the cables, the cable forces are related to displacements on the two sides of the cables as follows:

$$\xi_{[4 \times 1]} = k(x_{[4 \times 1]} - q_{[4 \times 1]}) \quad (11)$$

where k is the elastic constant of the cables in N/m, a measure of stiffness (assuming all cables are similar).

Using equations (10) and (11) we obtain:

$$\theta_{[3 \times 1]} = B^{-T} \cdot (x_{[4 \times 1]} - k^{-1} \xi_{[4 \times 1]}) \quad (12)$$

Here $\theta_{[3 \times 1]}$ is the vector of actual joint angles. On the other hand, since $x_{[4 \times 1]}$ is the cable displacement at the proximal end, $B^{-T} x_{[4 \times 1]}$ is the joint angle vector that we think we are achieving, using proximal measurements. The difference between the actual joint angles in eq. (12) and these angles (that we think are achieving) are the joint angle errors, as follows:

$$\theta_{e[3 \times 1]} = B^{-T} \cdot x_{[4 \times 1]} - \theta_{[3 \times 1]} = k^{-1} B^{-T} \xi_{[4 \times 1]} \quad (13)$$

From this equation, it is evident that the tracking error is inversely proportional to stiffness k.

To see how friction affects tracking error, we need to convert the cable forces to joint torques using eq. (3):

$$\theta_{e[3 \times 1]} = k^{-1} B^{-T} \xi_{[4 \times 1]} = k^{-1} B^{-T} B^{-1} \cdot \tau_{[3 \times 1]} = k^{-1} (BB^T)^{-1} \tau_{[3 \times 1]} \quad (14)$$

where it is noted that $BB^T$ is a nonsingular square matrix of size 3×3. Moreover, $\tau_{[3 \times 1]}$ is the vector of joint torques—see eq. (6).

Figure 4:
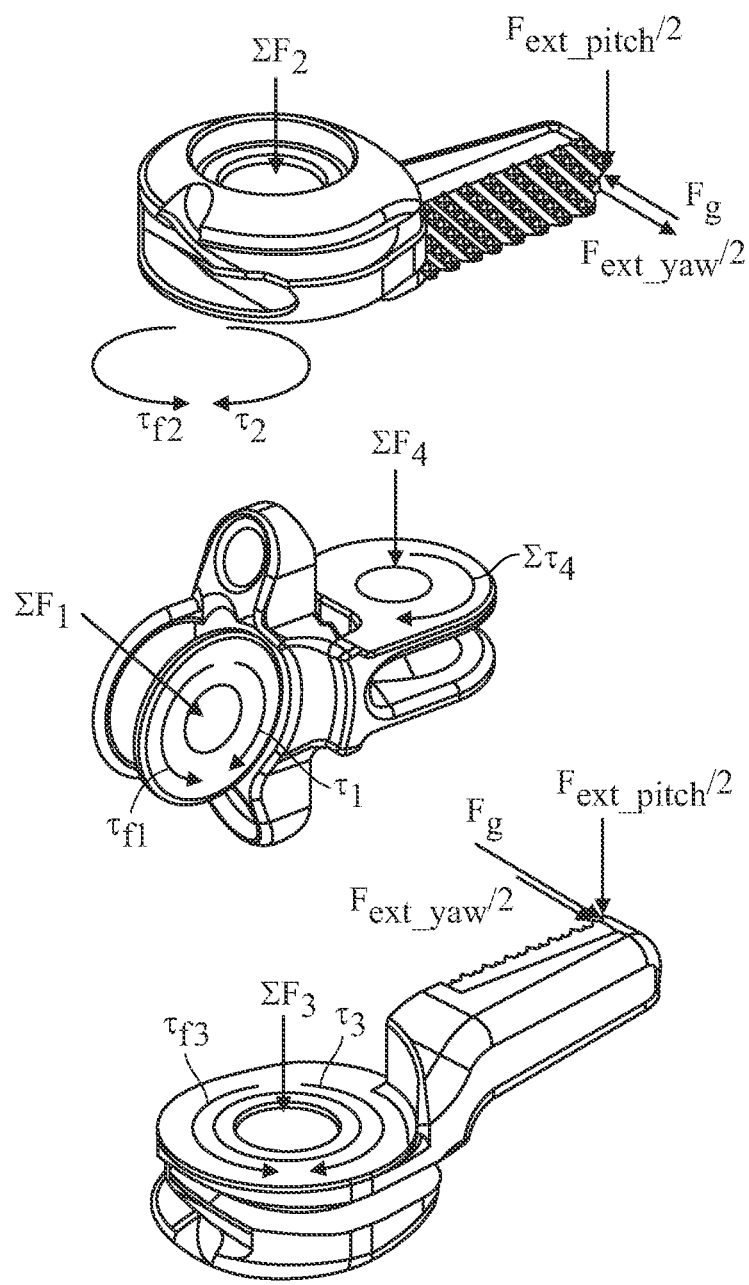
FIG. 4 shows free body diagrams of the pair of jaws and its robotic wrist (for pitch degree of freedom.)

In order to progress further, we consider the case where there is grip force but no side load, although that does not affect the more general applicability of the case. That case is considered here only for ease of illustration of the broader concept. A free body diagram of the two jaws and the proximal wrist (for pitch degree of freedom, DOF) is shown in FIG. 4, where $\Sigma F_1$ to $\Sigma F_4$ and $\Sigma \tau_4$ are the composite reaction forces and torque at the joints, $\tau_{f1}$ is friction at the pitch joint, and $\tau_{f2}$ and $\tau_{f3}$ are the joint frictions for Jaw1 and Jaw2, respectively. Moreover, $F_g$ is the grip force between the two jaws, and $\tau_i$ are the joint torques. Finally, $F_{ext\_pitch}$ and $F_{ext\_yaw}$ are the external side loads applied at the jaw tips, and are assumed to be distributed evenly on both jaws.

The equation of motion of the proximal wrist around the pitch axis is as follows:

$$\tau_1 - \tau_{f1} - \tau_{ext\_pitch} = J_1(\theta) \ddot{\theta}_1 + C_1(\theta, \dot{\theta})_{[1 \times 3]} \dot{\theta}_{[3 \times 1]} + G_1(\theta) \quad (15)$$

where $\tau_{ext\_pitch}$ is the external wrench around the pitch axis caused by the external forces on the jaws.

For the jaws, the external load is usually applied through an object that is held between the jaws. Therefore, we assume each jaw takes half of the load. As a result, we get:

$$\tau_2 - LF_g - \tau_{f2} - \tau_{ext\_yaw}/2 = J_2(\theta) \ddot{\theta}_2 + C_2(\theta, \dot{\theta})_{[1 \times 3]} \dot{\theta}_{[3 \times 1]} + G_2(\theta) \quad (16)$$

$$\tau_3 + LF_g - \tau_{f3} - \tau_{external} - \tau_{ext\_yaw}/2 = J_3(\theta) \ddot{\theta}_3 + C_3(\theta, \dot{\theta})_{[1 \times 3]} \dot{\theta}_{[3 \times 1]} + G_3(\theta) \quad (17)$$

In Equations (15-17), the right hand side are composed of the inertial, Coriolis, centrifugal, and gravity terms. However, as the moving components (wrist and jaws) have very small masses and inertias, these terms are negligible compared to frictional and driving torques. As a result, the right hand side of equations (15-17) can be neglected. Therefore, we will get:

$$\begin{cases} \tau_1 - \tau_{f1} - \tau_{e\_pitch} = 0 \\ \tau_2 - LF_g - \tau_{f2} - \tau_{e\_yaw}/2 = 0 \\ \tau_3 + LF_g - \tau_{f3} - \tau_{e\_yaw}/2 = 0 \end{cases} \quad (18)$$

As a result, we find the vector of joint torques to be:

$$\tau = \begin{bmatrix} \tau_{f1} + \tau_{ext\_pitch} \\ \tau_{f2} + LF_g + \tau_{ext\_yaw}/2 \\ \tau_{f3} - LF_g + \tau_{ext\_yaw}/2 \end{bmatrix} \quad (19)$$

Substituting this back into eq. (14) we obtain:

$$\theta_{e[3\times 1]} = k^{-1}(BB^T)^{-1} = \begin{bmatrix} \tau_{f1} + \tau_{e\_pitch} \\ \tau_{f2} + LF_g + \tau_{ext\_yaw}/2 \\ \tau_{f3} - LF_g + \tau_{ext\_yaw}/2 \end{bmatrix} \quad (20)$$

Using eq. (2), the error angles in extrinsic coordinate system will be as follows:

$$\begin{bmatrix} \theta_{e\_pitch} \\ \theta_{e\_yaw} \\ \theta_{e\_jaw} \end{bmatrix} = D\theta_{e[3\times 1]} \quad (21)$$

Substituting eq. (20) we get:

$$\begin{bmatrix} \theta_{e\_pitch} \\ \theta_{e\_yaw} \\ \theta_{e\_jaw} \end{bmatrix} = k^{-1}D(BB^T)^{-1}\begin{bmatrix} \tau_{f1} + \tau_{e\_pitch} \\ \tau_{f2} + LF_g + \tau_{ext\_yaw}/2 \\ \tau_{f3} - LF_g + \tau_{ext\_yaw}/2 \end{bmatrix} \quad (22)$$

To separate the effect of friction and grip force on tracking error, the term in the parenthesis can be decomposed further as follows:

$$\begin{bmatrix} \theta_{e\_pitch} \\ \theta_{e\_yaw} \\ \theta_{e\_jaw} \end{bmatrix} = k^{-1}D(BB^T)^{-1}\begin{bmatrix} \tau_{f1} \\ \tau_{f2} \\ \tau_{f3} \end{bmatrix} + \quad (23)$$

$$k^{-1}D(BB^T)^{-1}\begin{bmatrix} 0 \\ +LF_g \\ -LF_g \end{bmatrix} + k^{-1}D(BB^T)^{-1}\begin{bmatrix} \tau_{ext\_pitch} \\ \tau_{ext\_yaw}/2 \\ \tau_{ext\_yaw}/2 \end{bmatrix}$$

The first term on the right hand side of the above equation captures the effect of friction on extrinsic joint angle errors and shows that the tracking error is linearly proportional to joint friction. The second and third terms capture the influence of grip and external loads on the tracking error.

Replacing B, and D from eq. (4), and (2.b) respectively, and assuming $r_{31}=r_{21}$, and $r_{32}=r_{22}$, we get:

$$\begin{bmatrix} \theta_{e\_pitch} \\ \theta_{e\_yaw} \\ \theta_{e\_jaw} \end{bmatrix} = \quad (24)$$

$$k^{-1}\begin{bmatrix} \frac{r_{21}^2+r_{22}^2}{2(r_{11}r_{22}+r_{12}r_{21})^2} & \frac{r_{12}r_{22}-r_{11}r_{21}}{2(r_{11}r_{22}+r_{12}r_{21})^2} & 0 \\ \frac{r_{12}r_{22}-r_{11}r_{21}}{2(r_{11}r_{22}+r_{12}r_{21})^2} & \frac{r_{11}^2+r_{12}^2}{2(r_{11}r_{22}+r_{12}r_{21})^2} & 0 \\ 0 & 0 & \frac{1}{r_{21}^2+r_{22}^2} \end{bmatrix}\begin{bmatrix} \tau_{f1} \\ \tau_{f2}+\tau_{f3} \\ \tau_{f2}-\tau_{f3} \end{bmatrix} +$$

$$k^{-1}\begin{bmatrix} 0 & 0 & 0 \\ 0 & 0 & 0 \\ 0 & 0 & \frac{2}{r_{21}^2+r_{22}^2} \end{bmatrix}\begin{bmatrix} 0 \\ 0 \\ LF_g \end{bmatrix} +$$

$$k^{-1}\begin{bmatrix} \frac{r_{21}^2+r_{22}^2}{2(r_{11}r_{22}+r_{12}r_{21})^2} & \frac{r_{12}r_{22}-r_{11}r_{21}}{2(r_{11}r_{22}+r_{12}r_{21})^2} & 0 \\ \frac{r_{12}r_{22}-r_{11}r_{21}}{2(r_{11}r_{22}+r_{12}r_{21})^2} & \frac{r_{11}^2-r_{12}^2}{2(r_{11}r_{22}+r_{12}r_{21})^2} & 0 \\ 0 & 0 & 0 \end{bmatrix}\begin{bmatrix} \tau_{ext\_pitch} \\ \tau_{ext\_yaw} \\ 0 \end{bmatrix}$$

Several observations can be made from equation (24). As can be seen, the pitch and yaw tracking errors due to friction are only affected by $\tau_{f1}$, and $\tau_{f2}+\tau_{f3}$. On the other hand, the tracking error for jaw DOF is only affected by $\tau_{f2}-\tau_{f3}$. It is also observed that, as expected, the grip force only affects the jaw DOF. However, we know that during grip application, the jaw is closed. So the actual measured jaw angle should be zero (or should be the jaw closure angle at contact). What is represented in second term of eq. (20) is the additional amount we read (as joint status) when the jaws are closed. For joint angle estimation purposes, this value needs to be subtracted from the estimated jaw angle found purely based on cable displacements and inverse kinematics. Moreover, we can consider an approximation/simplification for the case that a grip force is being applied. In this case, since the jaws are moving in the same direction, and same speed, and the forces on the jaw pins are very similar, the joint friction values will be also similar. As a result, we can assume $\tau_{f2}-\tau_{f3}\approx 0$, in this special case.

Additionally, from the third term on the right hand side of Eq. (24) we observe that $\tau_{ext\_pitch}$, and $\tau_{ext\_yaw}$ affect the tracking error very similarly to $\tau_{f1}$, and $\tau_{f2}+\tau_{f3}$. The essentially play a similar role in providing a resistive force on the distal end of the device. Without knowing the magnitudes of the external loads, and without any distal sensors, they are essentially indistinguishable from joint frictions.

As seen in Eq. (24), the joint friction values (e.g., Tauf1 which is friction torque at the pitch joint, and Tauf2 and Tauf3 which are joint frictions for Jaw1 and Jaw2, respectively) are required for calculating the end-effector tracking errors. The friction in the joints are proportional to the normal forces on the joint pins. These forces can change with the magnitude of grip or external loads on the jaws, thereby changing the amount of friction. In what follows, we seek a relationship between the frictional forces/torques and the cable forces, where the cable forces can be measured using sensors.

As defined in eq. (6), the driving torques can be expressed, using eq. (3), as a function of cable forces:

$$\begin{cases} \tau_1 = -r_{11}\xi_1 - r_{12}\xi_2 + r_{11}\xi_3 + r_{12}\xi_4 \\ \tau_2 = -r_{21}\xi_1 + r_{22}\xi_2 \\ \tau_3 = r_{31}\xi_3 - r_{32}\xi_4 \end{cases} \quad (25)$$

Solving equations (25) to eliminate the driving torques, and assuming $r_{21}=r_{31}$, and $r_{22}=r_{32}$, we get:

$$\begin{cases} \tau_{f1} = -r_{11}(\xi_1-\xi_3) - r_{12}(\xi_2-\xi_4) - \tau_{ext\_pitch} \\ \tau_{f2}+\tau_{f3} = -r_{21}(\xi_1-\xi_3) + r_{22}(\xi_2-\xi_4) - \tau_{ext\_yaw} \\ \tau_{f2}-\tau_{f3} = -r_{21}(\xi_1+\xi_3) + r_{22}(\xi_2-\xi_4) - 2LF_g \end{cases} \quad (26)$$

As discussed above, in the case the jaws are grasping an object and moving together, we have $\tau_{f2} - \tau_{f3} \approx 0$. Using the third equation in eq. (26), we arrive at an equation that can be used for estimating the grip force:

$$F_g = \frac{-r_{21}(\xi_1 + \xi_3) + r_{22}(\xi_2 + \xi_4)}{2L} \qquad (27)$$

Figure 5:
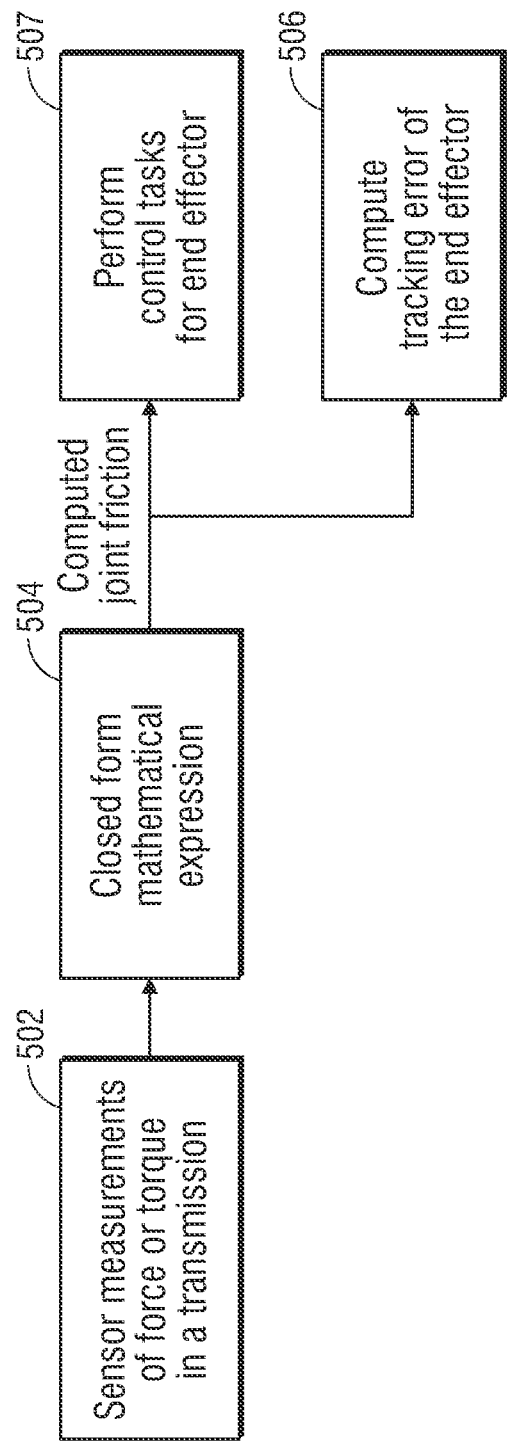
FIG. 5 is a block diagram of a method for estimating joint friction in a joint of a robotic wrist.

Referring now to FIG. 5 which is a block diagram of a method for estimating joint friction in a joint of a robotic wrist, once cable force measurements are available (by producing (502) sensor measurements of force in the transmission, that mechanically couples the robotic wrist to its actuator), the joint friction torques can be computed (504) from equations (26), which is a closed form mathematical expression that relates transmission force or torque variables Zeta1, Zeta2, Zeta3, Zeta4 to joint friction variables Tauf1, Tauf2, Tauf3 for joints of the end effector. The so-computed joint friction values can then be replaced back into Eq. (24) which is a closed form mathematical expression that relates the joint friction variable to the tracking error, e.g., used to compute (506) the estimated tracking errors $\theta_{e\_pitch}$ $\theta_{e\_yaw}$ $\theta_{e\_jaw}$ of the end effector. The designer can then determine suitable values for cable stiffness (k), or may decide to reduce friction torques (e.g., by lubrication, or using different materials), as ways to reduce the tracking error. The computed joint friction values can also be used to perform control tasks (507) for the end effector to mimic movement of a user input device.

While certain aspects have been described above and shown in the accompanying drawings, it is to be understood that such descriptions are merely illustrative of and not restrictive on the invention, and that the invention is not limited to the specific constructions and arrangements shown and described, since various other modifications may occur to those of ordinary skill in the art. For example, while the above description illustrates the method of estimating joint friction using a wristed pair of pivoting jaws, and in particular the joint friction associated with controlling the jaw angle and pitch and yaw of a surgical robotic wrist, the method is also applicable to estimating joint friction in other types of surgical robotic end effectors, e.g., needle drivers. The description is thus to be regarded as illustrative instead of limiting.

What is claimed is:

1. A computerized method for controlling movement of an end effector having a robotic wrist, the method comprising the following operations performed by a computer system:
   producing sensor measurements of force or torque in a transmission that mechanically couples the robotic wrist to an actuator, wherein the sensor measurements are cable force measurements;
   estimating joint friction in a joint of the robotic wrist, based on the cable force measurements, by relating the cable force measurements to a joint friction variable; and
   performing control tasks to control movement of the end effector, by using the estimated joint friction.

2. The method of claim 1 wherein performing control tasks comprises
   generating one or more control signals which control how the actuator is energized to move the robotic wrist.

3. The method of claim 2 wherein the cable force measurements are measurements of force or tension on a plurality of cables that are part of the transmission.

4. The method of claim 2 wherein using the estimated joint friction comprises
   computing a tracking error of the end effector based on the joint friction variable; and
   adjusting the one or more control signals based on the tracking error.

5. The method of claim 4 further comprising
   computing the tracking error using a mathematical expression that relates the joint friction variable to the tracking error.

6. The method of claim 4 wherein relating the cable force measurements to the joint friction variable comprises relating a plurality of cable tension variables to a plurality of joint friction torque variables, wherein the plurality of joint friction torque variables represent friction at a plurality of joints of the end effector.

7. The method of claim 1 wherein the end effector comprises a pivoting jaw having a jaw angle and being mechanically coupled to the wrist to be driven by the actuator, and the tracking error refers to the jaw angle.

8. The method of claim 7 wherein the joint friction variable represents friction at the joint of the wrist.

9. The method of claim 8 wherein the cable force measurements are measurements of force or tension on a plurality of cables that are part of the transmission that mechanically couples the robotic wrist to the actuator.

10. The method of claim 1 wherein relating the cable force measurements to the joint friction variable comprises relating a plurality of cable tension variables to a plurality of joint friction torque variables, wherein the plurality of joint friction torque variables represent friction at a plurality of joints of the end effector.

11. An article of manufacture comprising a computer-readable storage medium having stored therein instructions that configure a processor to:
    produce sensor measurements of force or torque in a transmission, wherein the transmission mechanically couples a robotic wrist of an end effector to an actuator so the actuator can drive a joint of the robotic wrist and the sensor measurements are cable force measurements;
    estimate joint friction in the joint of the robotic wrist based on the cable force measurements, by relating the cable force measurements to a joint friction variable; and
    perform control tasks to control movement of the end effector, by using the estimated joint friction.

12. The article of manufacture of claim 11 wherein the computer-readable storage medium has stored therein instructions that configure the processor to use the estimated joint friction by computing a tracking error of the end-effector based on the joint friction variable.

13. The article of manufacture of claim 12 wherein the processor performs the control tasks by generating one or more control signals which control how the actuator is energized to move the robotic wrist, based on the tracking error.

14. The article of manufacture of claim 13 wherein the cable force measurements are measurements of force or tension on a plurality of cables that are part of the transmission.

15. The article of manufacture of claim 13 wherein the processor relates the cable force measurements to the joint friction variable by relating a plurality of cable tension variables to a plurality of joint friction torque variables, wherein the plurality of joint friction torque variables represent friction at a plurality of joints of the end effector.

16. The article of manufacture of claim 13 wherein the end effector comprises a jaw having a jaw angle and being mechanically coupled to the robotic wrist, and the tracking error refers to the jaw angle.

17. The article of manufacture of claim 16 wherein the joint friction variable represents friction at the joint of the robotic wrist.

18. The article of manufacture of claim 17 wherein the cable force measurements are measurements of force or tension on a plurality of cables that are part of the transmission that mechanically couples the robotic wrist to the actuator.

19. The article of manufacture of claim 11 wherein processor relates the cable force measurements to the joint friction variable comprises by relating a plurality of cable tension variables to a plurality of joint friction torque variables, wherein the plurality of joint friction torque variables represent friction at a plurality of joints of the end effector.

20. The article of manufacture of 19 wherein the computer-readable storage medium has stored therein further instructions that configure the processor to use the estimated joint friction by computing a tracking error of the end effector based on the joint friction variable.

* * * * *